US006498162B1

United States Patent
Esser et al.

(10) Patent No.: US 6,498,162 B1
(45) Date of Patent: Dec. 24, 2002

(54) ARYLGLYCINAMIDE DERIVATIVES, METHOD OF PRODUCING SAID DERIVATIVES AND PHARMACEUTICAL COMPOSITIONS CONTAINING THESE COMPOUNDS

(75) Inventors: Franz Esser, Ingelheim (DE); Gerd Schnorrenberg, Gau-Algesheim (DE); Kurt Schromm, Ingelheim (DE); Horst Dollinger, Ingelheim (DE); Birgit Jung, Schwabenheim (DE); Georg Speck, Ingelheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/703,758

(22) Filed: Nov. 1, 2000

Related U.S. Application Data

(63) Continuation of application No. 09/142,271, filed as application No. PCT/EP97/01038 on Mar. 3, 1997, now abandoned.

(30) Foreign Application Priority Data

Mar. 6, 1996 (DE) .......................... 196 08 665

(51) Int. Cl.⁷ .................... A61K 31/535; A61K 31/495; C07D 241/04; C07D 403/00; A61P 25/00
(52) U.S. Cl. .............. 514/252.12; 514/235.8; 514/252.02; 514/252.11; 514/252.14; 514/253.01; 514/254.01; 514/255.02; 514/255.04; 544/121; 544/238; 544/295; 544/357; 544/360; 544/372; 544/377; 544/382; 544/384; 544/400
(58) Field of Search .................. 514/235.8, 252.02, 514/252.11, 252.12, 252.14, 253.01, 254.01, 255.02, 255.04; 544/121, 238, 295, 357, 360, 372, 377, 382, 384, 400

(56) References Cited

U.S. PATENT DOCUMENTS 3,033,869 A * 5/1962 Giudicelli et al. .......... 260/294

FOREIGN PATENT DOCUMENTS

DE 195 19 245 * 10/1996

OTHER PUBLICATIONS

Nagarajan et al., A Novel Displacement Reaction on .alpha.–Chlorodiphenylacetamides, Tetrahedron Letters, vol. 15, pp. 1387–1390, 1967.*

* cited by examiner

Primary Examiner—Brenda Coleman
(74) Attorney, Agent, or Firm—Robert P. Raymond; Timothy X. Witkowski; Mary-Ellen Devlin

(57) ABSTRACT

The invention relates to new arylglycinamide derivatives of general formula I

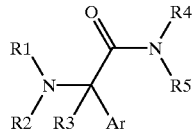

and the pharmaceutically acceptable salts thereof, wherein $R^1$ and $R^2$ together with the N to which they are bound form a ring of the formula

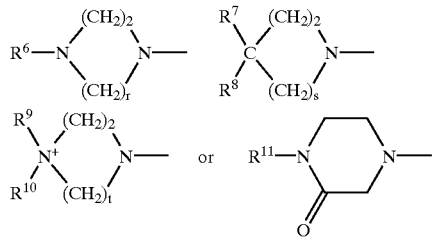

in which
$R^3$, $R^4$, $R^5$, Ar, $R^6$, $R^7$, $R^8$, $R^9$, $R^{10}$, $R^{11}$, r, s and t have the meanings given in the specification and the preparation and use thereof. The new compounds are valuable neurokinin (tachykinin) antagonists.

23 Claims, No Drawings

ARYLGLYCINAMIDE DERIVATIVES, METHOD OF PRODUCING SAID DERIVATIVES AND PHARMACEUTICAL COMPOSITIONS CONTAINING THESE COMPOUNDS

RELATED APPLICATIONS

This application is a continuation of application Ser. No. 09/142,271, filed Nov. 30, 1998, now abandoned, which is a national stage entry under 35 U.S.C. §371 of PCT/EP97/01038, filed Mar. 3, 1997.

SUMMARY OF THE INVENTION

The invention relates to new arylglycinamide derivatives of general formula

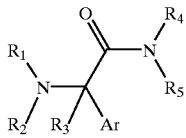

I and the pharmaceutically acceptable salts thereof, processes for preparing them and pharmaceutical compositions containing these compounds. The compounds are valuable neurokinin (tachykinin) antagonists.

The abbreviations used in this specification and claims are explained as follows:

CDI=Carbonyldiimidazole
DCCI=Dicyclohexylcarbodiimide
HOBt=1-Hydroxybenzotriazole
THF=Tetrahydrofuran
DMF=Dimethylformamide
RT=Room temperature
DMAP=4-Dimethylaminopyridine
TBTU=O-Benzotriazolyl-tetramethyluronium-tetrafluoroborate The formulae are shown in simplified form. In representing the compounds, for example, all the $CH_3$-substituents are represented by a hyphen and CH is represented by , thus, for example:

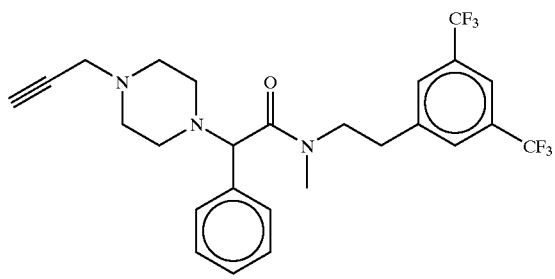

denotes

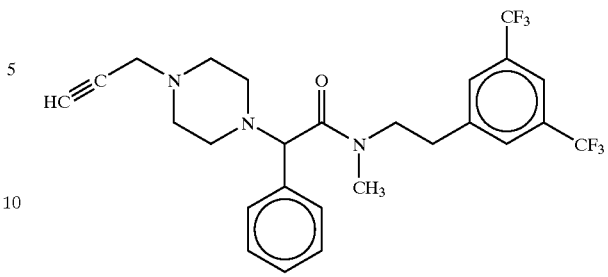

The invention relates to new arylglycinamide derivatives of general formula I

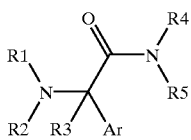

I or the pharmaceutically acceptable salts thereof, wherein
  Ar denotes unsubstituted or mono- to penta-substituted phenyl, or unsubstituted or mono- or disubstituted naphthyl [wherein the substituents of the phenyl and naphthyl independently of one another denote halogen (F, Cl, Br, I), $(C_{1-4})$alkyl, O—$(C_{1-4})$alkyl, $CF_3$, $OCF_3$ or $NR^{12}R^{13}$ (wherein $R^{12}$ and $R^{13}$ independently of one another denote H, methyl or acetyl)] or Ar is phenyl substituted by —O—$CH_2$—O— or —O—$(CH_2)_2$—O—;
  $R^1$ and $R^2$ together with the N to which they are bound denote a ring of the formula

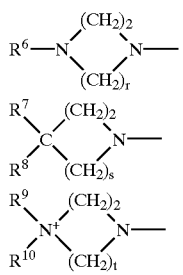

or

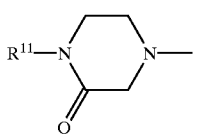

wherein
  r, s and t are 2 or 3;
  $R^6$ denotes
    H.
    $(C_{1-5})$alkyl,
    $(C_{3-5})$alkenyl
    propynyl,
    hydroxy $(C_{2-4})$alkyl,
    methoxy$(C_{2-4})$alkyl,
    di $(C_{1-3})$alkylamino $(C_{2-4})$alkyl, amino ($C_{2-4}$)alkyl,
amino,
di($C_{1-3}$)alkylamino,
monofluoro- to perfluoro($C_{1-2}$)alkyl,
N-methylpiperidinyl,
pyridyl,
pyrimidinyl,
pyrazinyl,
pyridazinyl
or the group —$CH_2$—$C(O)NR^{14}R^{15}$,
wherein
$R^{14}$ is H or ($C_{1-4}$)alkyl and
$R^{15}$ is H, ($C_{1-4}$)alkyl, ($C_{3-6}$)cycloalkyl, hydroxy($C_{2-4}$)alkyl, alkoxy($C_{2-3}$)alkyl, phenyl($C_{1-4}$)alkyl, or $R^{14}$ and $R^{15}$ together with the N to which they are bound form a ring (1-pyrrolidinyl, piperidino, morpholino or 1-methylpiperazin-4-yl);
$R^7$ has one of the definitions (a) to (d),
(a) hydroxy
(b) 4-piperidinopiperidyl,
(c)

wherein $R^{16}$ and $R^{17}$ independently of one another denote
H,
($C_{1-4}$)alkyl,
($C_{3-6}$)cycloalkyl,
hydroxy ($C_{2-4}$)alkyl,
($C_{1-3}$) alkoxy($C_{2-4}$)alkyl,
phenyl($C_{1-4}$)alkyl or
di($C_{1-3}$)alkylamino($C_{2-4}$)alkyl,
or if $R^{16}$ is H or ($C_{1-4}$)alkyl,
$R^{17}$ may also be —$CH_2C(O)NR^{18}R^{19}$, wherein $R^{18}$ and $R^{19}$ are defined as $R^{14}$ and $R^{15}$ hereinbefore;
(d)

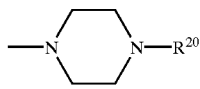

wherein $R^{20}$ denotes
H,
($C_{1-4}$)alkyl,
($C_{4-6}$)cycloalkyl or
—$CH_2C(O)NR^{21}R^{22}$,
wherein $R^{21}$ and $R^{22}$ are defined as $R^{14}$ and $R^{15}$ hereinbefore;
$R^8$ is H
$R^9$ and $R^{10}$ independently of each other denote ($C_{1-4}$) alkyl;
$R^{11}$ denotes
H,
($C_{1-5}$)alkyl,
($C_{3-5}$)alkenyl,
propynyl,
hydroxy($C_{2-4}$)alkyl,
methoxy($C_{2-3}$)alkyl,
di ($C_{1-3}$)alkylamino ($C_{2-3}$)alkyl,
amino($C_{2-3}$)alkyl,
amino,
di($C_{1-3}$)alkylamino,
monofluoro- to perfluoro ($C_{1-2}$)alkyl,
N-methylpiperidinyl,
pyridyl,
pyrimidinyl,
pyrazinyl,
pyridazinyl
or the group —$CH_2$—$C(O)NR^{23}R^{24}$,
wherein $R^{23}$ and $R^{24}$ are defined as $R^{14}$ and $R^{15}$ hereinbefore;
$R^3$ denotes H, ($C_{1-4}$)alkyl, unsubstituted or mono- to trisubstituted phenyl, wherein the substituents independently of one another denote halogen (F, Cl, Br, I), ($C_{1-4}$)alkyl, O—($C_{1-4}$)alkyl, $CF_3$, $OCF_3$ or $NR^{25}R^{26}$ (wherein $R^{25}$ and $R^{26}$ independently of one another denote H, methyl or acetyl);
$R^4$ denotes phenyl($C_{1-4}$)alkyl or naphthyl($C_{1-4}$)alkyl, wherein phenyl may be substituted by 1 to 3 substituents, wherein the substituents independently of one another denote halogen (F, Cl, Br, I), ($C_{1-4}$)alkyl, O—($C_{1-4}$)alkyl, $CF_3$, $OCF_3$ or $NR^{27}R^{28}$ (wherein $R^{27}$ and $R^{28}$ independently of one another denote H, methyl or acetyl); and
$R^5$ denotes H, ($C_{1-4}$)alkyl, ($C_{3-6}$)cycloalkyl, $CH_2COOH$, $CH_2C(O)NH_2$, OH or phenyl($C_{1-4}$)alkyl.
Preferred compounds of general formula I are those wherein
Ar denotes unsubstituted or mono- or disubstituted phenyl, or unsubstituted naphthyl, or Ar is phenyl substituted by —O—$CH_2$—O— or —O—($CH_2$)$_2$—O—;
$R^1$ and $R^2$ together with the N to which they are bound denote a ring of the formula

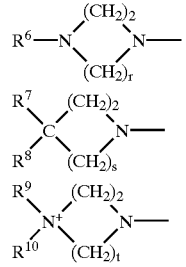

or

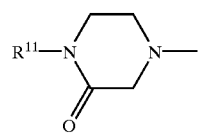

wherein
r is 2 or 3 and
s and t are 2;
$R^6$, $R^7$, $R^8$, $R^9$, $R^{10}$ and $R^{11}$ are as hereinbefore defined;
$R^3$ is H or ($C_{1-4}$)alkyl,
$R^4$ denotes phenyl($C_{1-4}$)alkyl or naphthyl($C_{1-4}$)alkyl, wherein phenyl may be substituted by 1 or 2 substituents, wherein the substituents independently of one another are halogen (F, Cl, Br, I), ($C_{1-4}$)alkyl, O—($C_{1-4}$)alkyl, $CF_3$ or $OCF_3$; and
$R^5$ denotes H, ($C_{1-4}$)alkyl, ($C_{3-6}$)cycloalkyl, OH or ($C_{1-4}$) alkylphenyl.
Particular mention should be made of compounds of formula I wherein Ar is unsubstituted or mono- or disubstituted phenyl, or unsubstituted naphthyl [wherein the substituents of the phenyl independently of one another are halogen (F, Cl, Br, I), methyl, methoxy, $CF_3$ or $OCF_3$] or Ar is phenyl substituted by —O—$CH_2$—O— or —O—($CH_2$)$_2$—O—;

particularly those wherein Ar is phenyl, naphthyl, phenyl substituted in position 3 and/or 4 by methoxy or halogen, or phenyl in which positions 2 and 3 or 3 and 4 are linked by —O—$CH_2$—O—, preferably those compounds wherein Ar is phenyl,
  phenyl substituted by methoxy in positions 3 and 4 or
    phenyl wherein positions 3 and 4 or 2 and 3 are linked by —O—$CH_2$—O—.

Of the compounds defined above, special mention should be made of those wherein, in the ring

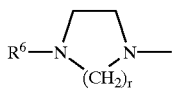

r is 2 or 3 and
$R^6$ denotes
  H,
  $(C_{1-5})$alkyl,
  $(C_{3-5})$alkenyl,
  propynyl,
  hydroxy $(C_{2-4})$alkyl,
  methoxy $(C_{2-4})$alkyl,
  di$(C_{1-3})$alkylamino$(C_{2-4})$alkyl,
  amino $(C_{2-4})$alkyl,
  amino,
  di$(C_{1-3})$alkylamino,
  monofluoro- to perfluoro$(C_{1-2})$alkyl,
  N-methylpiperidinyl,
  pyridyl,
  pyrimidinyl, or

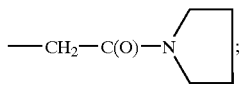

particularly those wherein
  r is 3 and $R^6$ is methyl;
and those wherein
  r is 2 and
  $R^6$ is
    H,
    $(C_{1-4})$alkyl,
    propenyl,
    propynyl,
    hydroxy $(C_{2-3})$alkyl,
    methoxyethyl,
    di$(C_{1-2})$alkylamino $(C_{2-3})$alkyl,
    aminoethyl,
    amino,
    dimethylamino,
    $CH_2CF_3$,
    N-methylpiperidinyl,
    pyridyl,
    pyrimidinyl, or

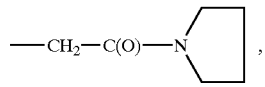

preferably those wherein
  r is 2 and
  $R^6$ is H, $(C_{1-3})$alkyl, allyl, 2-propynyl, —$CH_2CH_2OCH_3$, —$CH_2CH_2N(CH_3)_2$, N-methylpiperidinyl, 2-pyrimidinyl or

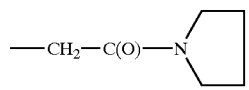

r is 2 and
  $R^6$ is H, $CH_3$, $C_3H_7$, $CH(CH_3)_2$, $CH_2CH_2OH$, $CH_2CH_2OCH_3$ or $CH_2CH_2N(CH_3)_2$.

Of the compounds defined above, mention should also be made of those wherein $R^1$ and $R^2$ together with the N to which they are bound form the ring

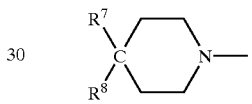

wherein $R^8$ is H and
  $R^7$ is OH

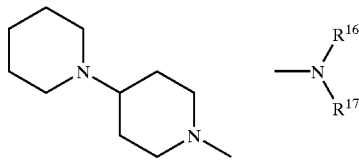

wherein $R^{16}$ and $R^{17}$ independently of one another denote:
  H
  $(C_{1-3})$alkyl,

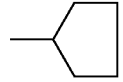

$(CH_2)_n$OH wherein n is 2, 3 or 4
$(CH_2)_2OCH_3$
—$(CH_2)_n$Ph wherein n is 2 or 4
$(CH_2)_2N(CH_3)_2$

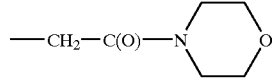

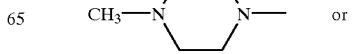 or

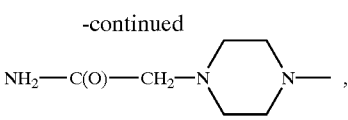

particularly those wherein
$R^{16}$ and $R^{17}$ are both $CH_3$ or $C_2H_5$ or
$R^{16}$ is H or $CH_3$ and $R^{17}$ is $(C_{1-3})$alkyl,

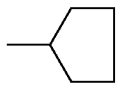

$(CH_2)_2OH$,
$(CH_2)_4OH$ or

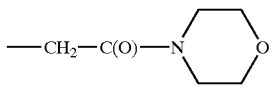

and those wherein
$R^7$ denotes

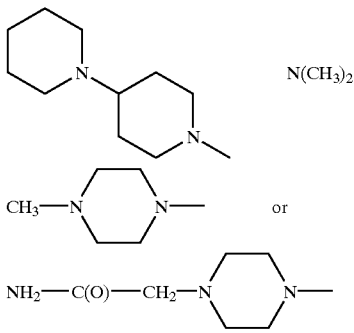

especially those wherein
$R^1$ and $R^2$ together with the N to which they are bound form the ring

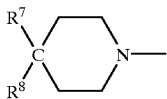

wherein
(a) $R^8$ is H and
$R^7$ is

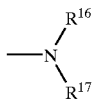

wherein $R^{16}$ and $R^{17}$ both represent $CH_3$, $C_2H_5$ or $CH_2CH_2OH$ or $R^{16}$ is H or $CH_3$ and $R^{17}$ is $(C_{1-3})$alkyl,

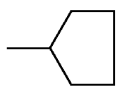

$(CH_2)_2OH$ or
$(CH_2)_4OH$ or
(b) $R^8$ is H and $R^7$ denotes

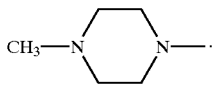

Of the compounds defined above, mention should also be made of those wherein
$R^1$ and $R^2$ together with the N to which they are bound form the ring

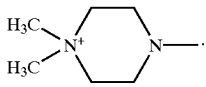

Of the compounds defined above, special mention should also be made of those wherein
$R^1$ and $R^2$ together with the N to which they are bound form the ring

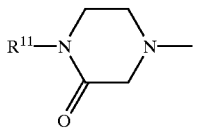

wherein $R^{11}$ is H or $(C_{1-3})$alkyl, particularly those wherein
$R^{11}$ is $—CH(CH_3)_2$ Of the compounds defined above, the ones of particular interest are those wherein $R^3$ is H; and/or
$R^4$ denotes phenyl$(C_{1-4})$alkyl, wherein phenyl may be substituted by 1 or 2 substituents, wherein the substituents independently of one another denote halogen (F, Cl, Br, I), $(C_{1-4})$alkyl, O—$(C_{1-4})$alkyl, $CF_3$ or $OCF_3$; and/or
$R^5$ denotes H, $(C_{1-4})$alkyl, $(C_{3-6})$cycloalkyl, —OH or phenyl$(C_{1-4})$alkyl,
particularly those wherein
$R^4$ denotes phenyl$(C_{2-4})$alkyl, wherein the substituents are in positions 3 and/or 5 of the phenyl ring and/or
$R^5$ is H, methyl, OH or phenethyl, preferably those wherein
$R^4$ is and $R^5$ is methyl.

Compounds of general formula I may have acid groups, chiefly carboxyl groups, and/or basic groups such as amino functions, for example. Compounds of general formula I may therefore be present either as internal salts, as salts with pharmaceutically acceptable inorganic acids such as hydrochloric acid, sulphuric acid, phosphoric acid, sulphonic acid or organic acids (such as maleic acid, fumaric acid, citric acid, tartaric acid or acetic acid) or as salts with pharmaceutically acceptable bases such as alkali or alkaline earth metal hydroxides or carbonates, zinc or ammonium hydroxides or organic amines such as dimethylamine, triethylamine, triethanolamine, etc.

The compounds according to the invention may occur as racemates but may also be obtained as pure enantiomers, i.e. in the (R)- or (S)-form.

The term naphthyl used hereinbefore includes both 1-naphthyl and 2-naphthyl.

DETAILED DESCRIPTION OF THE INVENTION

Test results for compounds according to the invention:

The receptor affinity for the $NK_1$-receptor (substance P-receptor) is determined on human lymphoblastoma cells (IM-9) with cloned $NK_1$-receptors, by measuring the displacement of $^{125}I$-labelled substance P. The $K_i$-values thus obtained show the efficacy of the compounds:

|  | Ki [nM] |
|---|---|
| Example 1 | 1.2 |
| Example 2 | 1.0 |
| Example 3 | 19 |
| Example 4 | 1.4 |
| Example 5 | 1.5 |
| Example 8 | 1.8 |
| Example 9 | 2.5 |
| Example 11 | 3.8 |
| Example 12 | 5.0 |
| Example 13 | 2.4 |
| Example 15 | 0.98 |
| Example 16 | 0.90 |
| Example 17 | 7.75 |
| Example 18 | 0.96 |
| Example 19 | 1.17 |
| Example 20 | 2.0 |
| Example 22 | 2.2 |
| Example 23 | 2.5 |
| Example 24 | 2.2 |
| Example 25 | 6.0 |
| Example 26 | 1.6 |
| Example 28 | 1.3 |
| Example 30 | 1.8 |
| Example 32 | 1.3 |
| Example 33 | 7.4 |
| Example 34 | 2.9 |
| Example 47 | 1.7 |
| Example 55 | 1.25 |
| Example 63 | 1.4 |
| Example 64 | 1.1 |
| Example 65 | 5.7 |
| Example 73 | 2.0 |
| Example 74 | 1.5 |
| Example 75 | 0.44 |
| Example 76 | 2.0 |

The compounds according to the invention are valuable neurokinin (tachykinin) antagonists which have both substance P antagonism and also neurokinin A and neurokinin B antagonistic properties. They are useful for the treatment and prevention of neurokinin-mediated diseases:

for the treatment or prevention of inflammatory and allergic diseases of the respiratory tract, such as asthma, chronic bronchitis, hyperreactive respiratory tract, emphysema, rhinitis and cough, and of the eyes, such as conjunctivitis and iritis, of the skin, such as dermatitis in contact eczema, urticaria, psoriasis, sunburn, insect bites and stings, itching, sensitive or hypersensitive skin, of the gastrointestinal tract, such as gastric and duodenal ulcers, ulcerative colitis, Crohn's disease, irritable bowel and Hirschsprung's disease, of the joints, such as rheumatoid arthritis, reactive arthritis and Reiter syndrome;

for treating diseases of the central nervous system such as dementia, Alzheimer's disease, schizophrenia, psychoses, depression, headache (e.g. migraine or tension headaches), epilepsy, Parkinson's disease and stroke;

for treating herpes zoster and postherpetic pain, tumours, collagenoses, dysfunction of the deferent urinary tract, haemorrhoids, nausea and vomiting, caused for example by radiation or cytostatic therapy or motion and pain of all kinds.

The invention therefore also relates to the use of the compounds according to the invention as therapeutic agents and pharmaceutical preparations which contain these compounds. They are preferably used in humans. The compounds according to the invention may be administered by intravenous, subcutaneous, intramuscular, intraperitoneal or intranasal route, by inhalation, by transdermal route, optionally aided by iontophoresis or enhancers known from the literature, and by oral route.

For parenteral administration the compounds of formula I or the physiologically acceptable salts thereof, possibly with the conventional substances such as solubilisers, emulsifiers or other adjuvants, are dissolved, suspended or emulsified. Solvents which may be used include: water, physiological saline solutions or alcohols, e.g. ethanol, propanediol or glycerol, sugar solutions such as glucose or mannitol solutions or a mixture of several solvents.

In addition, the compounds may be administered by means of implants, e.g. of polylactide, polyglycolide or polyhydroxybutyric acid or intranasal preparations.

The oral efficacy of compounds of general formula I can be demonstrated by the following standard test:

Inhibition of lowering of blood pressure caused by $NK_1$ in anaesthetised guinea pigs.

Guinea pigs weighing 300–500 grams were anaesthetised with pentobarbital (50 mg/kg i.p.), intubated and artificially ventilated. They were ventilated with 10 ml/kg of air at a frequency of 60 breaths per minute. The carotid artery was canulated and the arterial blood pressure was recorded. A polyethylene tube was inserted into the jugular vein for the intravenous supply of substances.

A temporary reduction in blood pressure was brought about at intervals of 10 minutes by intravenous administration of the $NK_1$-agonist $[(\beta Ala^4, Sar^9, Met (O_2)^{11}]SP (4–11)$

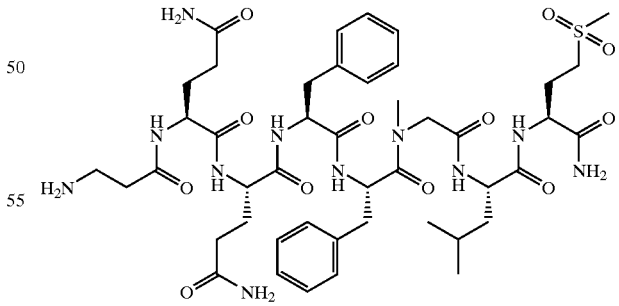

in a dose of 0.2 μmol/kg. After the blood pressure thus produced has been measured, the test compound was introduced into the duodenum and the $NK_1$-agonist was again injected every 10 minutes.

The results were expressed as a % inhibition of the reduction in blood pressure caused by the $NK_1$-agonist specified.

In a dosage of 1 mg/kg (administered into the duodenum) the compound of Example 1 inhibited the lowering of blood pressure caused by the $NK_1$-agonist by 80%.

The compounds according to the invention can be produced using generally known methods.

The compounds may be prepared in various ways. The two most common procedures are represented by the following diagram:

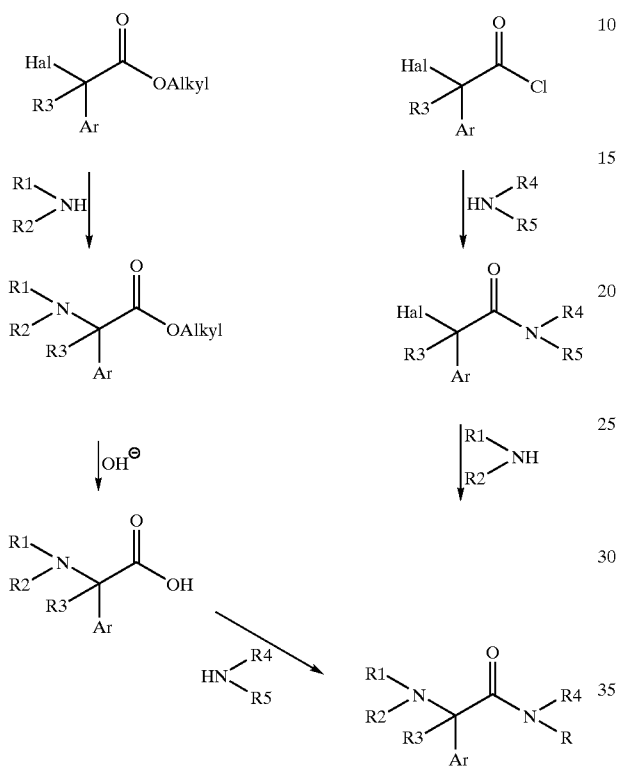

Method A. The carboxylic acid may be linked to the amine $HN(R^5)R^4$ by various methods. Conventional methods are coupling processes such as those used in peptide chemistry. A coupling reagent such as TBTU, DCCI/HOBt, CDI, etc., is added to the coupling partners in substantially equivalent quantities. Suitable solvents are DMF, THF, $CH_2Cl_2$, $CHCl_3$, acetonitrile or other inert solvents or mixtures thereof. The suitable temperature range is between −50° C. and +120° C., preferably between 0° C. and 40° C.

The carboxylic acid may also initially be converted into the corresponding acid halide by known methods using $SOCl_2$, $SO_2Cl_2$, $PCl_3$, $PCl_5$ or $PBr_3$ or mixtures thereof, and the acid halide is then reacted with the amine $HN(R^5)R^4$ in an inert solvent such as $CH_2Cl_2$, THF or dioxane at temperatures between −50° C. and +100° C., typically at 0° to 20° C.

Another alternative is to convert the carboxylic acid initially into the alkylester, usually the methylester, by known methods and this ester is then reacted with the amine $HN(R^5)R^4$ in an inert solvent such as DMF, dioxane or THF. The reaction temperatures are between 20° C. and 150° C., typically between 50° C. and 120° C. The reaction may also be carried out in a pressurized container.

Method B. Here, the α-halo-arylacetamide derivative obtained by known methods is reacted with the amine $R^1(R^2)NH$, thereby cleaving hydrogen halide. Inorganic bases such as $K_2CO_3$, $NaHCO_3$ or $CaCO_3$ or organic bases such as triethylamine, Hünig base, pyridine or DMAP are used to mop up the cleaved (or excess) hydrogen halide, or an excess of the amine $R^1(R^2)NH$ may be used. DMF, THF, dioxane or other inert solvents are used. The temperature range for the reaction is from 0 to 100° C., typically between 10 and 80° C.

Method C. The compounds according to the invention wherein $R^5$ is not H may also be prepared as follows: first of all, the corresponding compound in which $R^5$ is H is synthesised using method A or B. Then, N-alkylation is carried out as follows in order to introduce alkyl, cycloalkyl or $CH_2COOH$. The compounds according to the invention wherein $R^5$ is H are deprotonated with an equivalent quantity of NaH, $NaNH_2$, KOH, $NaOCH_3$ or another strong base. Anhydrous inert solvents such as THF, dioxane or diethylether are used for this. Then the corresponding alkylating agent is added slowly in the form of the corresponding halide, tosylate or mesylate. The reaction is carried out at a temperature within the range from −50° C. to +100° C., typically between 0° C. and +5° C.

EXAMPLE 1

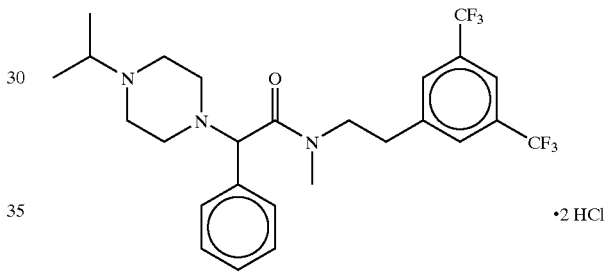

Mp.: 105-115° C.
FAB-MS: $(M+H)^+ = 516.3$.

1st step: 0.71 g of 1-isopropylpiperazine were dissolved in 55 ml of anhydrous DMF, mixed with 0.64 g of $Na_2CO_3$, stirred for 20 minutes at RT and then cooled to 5° C. 1.15 g of methyl (R,S)-α-bromophenylacetate were added and the suspension was stirred overnight at RT. The precipitate was filtered off and the filtrate was evaporated down. The residue was taken up in ethyl acetate, extracted twice with 10% $KHCO_3$ solution and once with saturated NaCl solution. The organic phase was dried over $Na_2SO_4$, filtered and evaporated down, to yield 1.23 g of methyl (R,S)-1-isopropyl-4-(2-phenylacetate) piperazine as a viscous oil.

Yield: about 89%.

2nd step: 1.23 g of the product from the 1st step were dissolved in 10 ml of methanol and 10 ml of THF, mixed with 10 ml of 1N NaOH and the mixture was stirred overnight at ambient temperature. The clear reaction solution was neutralised by the addition of 10 ml of 1N HCl, evaporated to dryness, the residue was treated with DMF and the solid was separated by suction filtering. The filtrate was evaporated down and the residue was triturated with ether, the solid substance removed by suction filtering and dried in a desiccator. In this way, 1.1 g of (R,S)-1-i-propyl-4-(2-phenylacetic acid)-piperazine were obtained as a solid white substance.
Yield: 92%.

3rd step: 0.37 g of the product of the 2nd step and 0.42 g of N-methyl-3,5-bis-(trifluoromethyl)-phenylethylamine were dissolved in 14 ml of DMF and adjusted to pH 8.5 by the addition of about 0.4 ml of TEA. 0.48 g of TBTU were added and the mixture was stirred overnight at room temperature. The clear reaction solution was evaporated down in vacuo, the residue was stirred with $NaHCO_3$ solution and extracted twice with ethyl acetate. The combined organic phases were filtered and the filtrate was evaporated down. The residue was chromatographed over silica gel using $CH_2Cl_2$/MeOH (9:1) as eluant. The uniform fractions obtained were evaporated down, dissolved in a little MeOH, acidified with ethereal HCl and evaporated down again. The residue was triturated with ether and dried in a desiccator. 0.58 g of (R,S)-1-i-propyl-4-[2-phenylacetic acid-N-methyl-N-(3,5-bistrifluoromethyl-phenylethyl)]-amide dihydrochloride were obtained as a solid white substance.
Yield: 75%.

The other compounds of the invention may be prepared analogously, e.g. the following:

EXAMPLE 2

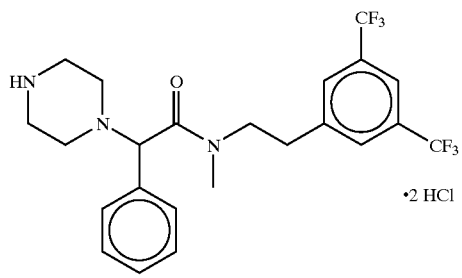

Mp. 141–146° C.
FAB-MS: (M+H) + = 474.3

EXAMPLE 3

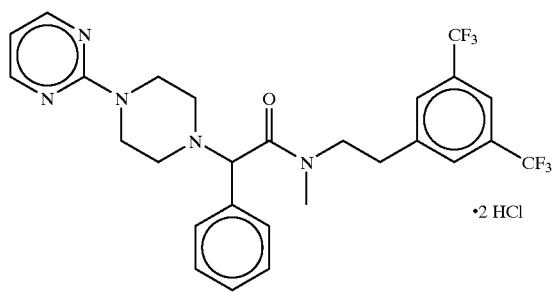

Mp.: 122–132° C.
FAB-MS: (M+H) + = 552.4

EXAMPLE 4

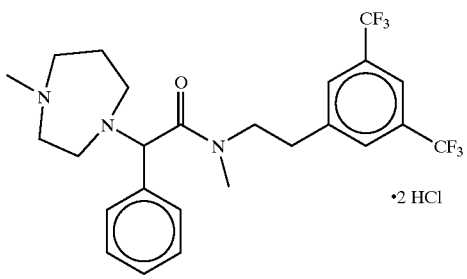

Mp.: 138–148° C.
FAB-MS: $(M+H)^+$ = 502.3

EXAMPLE 5

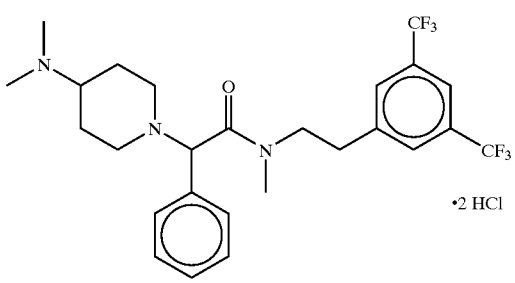

Mp.: 231–241° C. (Decomp.)
FAB-MS: $(M+H)^+$ = 516.4

EXAMPLE 6

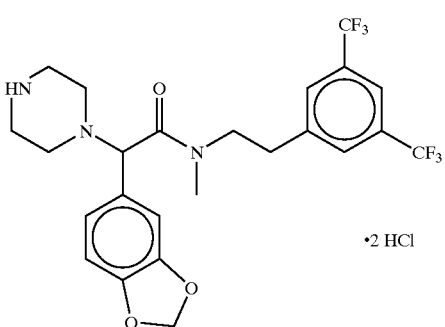

Mp.: 122–132° C.
FAB-MS: $(M+H)^+$ = 518.1

EXAMPLE 7
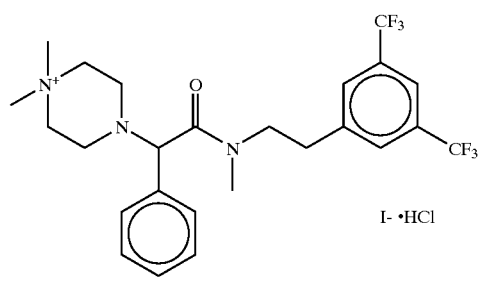
Mp.: 168–174° C. (Decomp.)
FAB-MS: M⁺ = 502.3
EXAMPLE 11
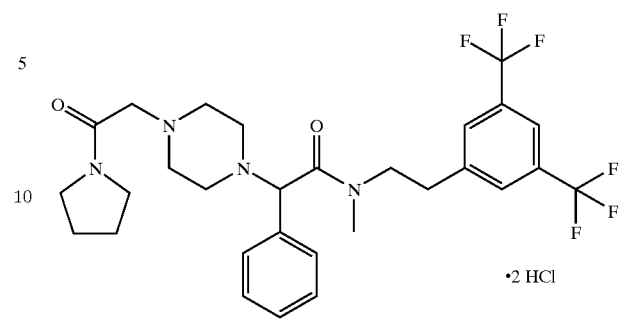
Bp.: 130–160° C.
Mp.: 215 - 218° C. (Decomp.)
EXAMPLE 8
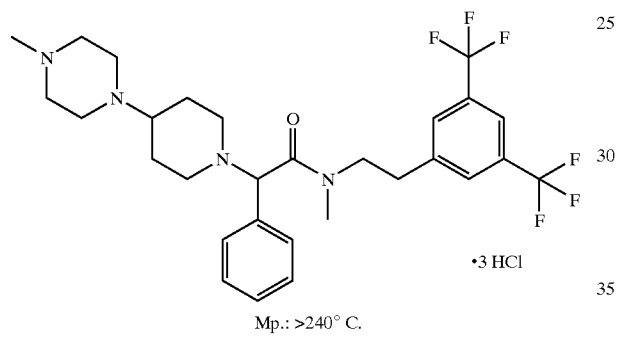
Mp.: >240° C.
EXAMPLE 12
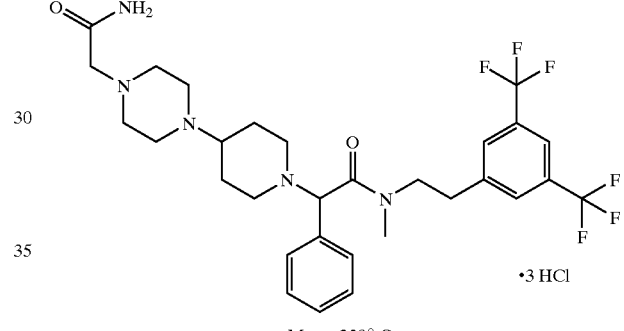
Mp.: >230° C.
EXAMPLE 9
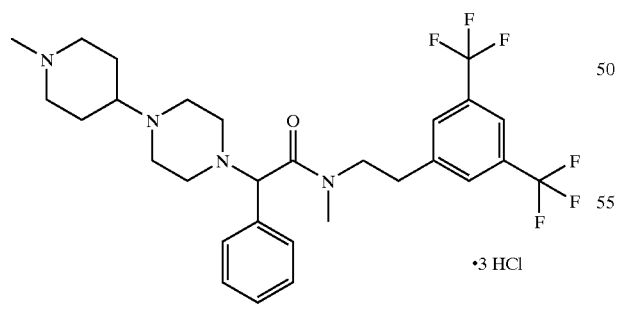
Mp.: >230° C.
EXAMPLE 13
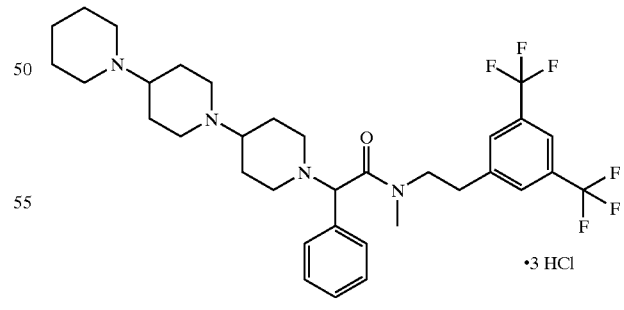
Mp.: >230° C.

EXAMPLE 15
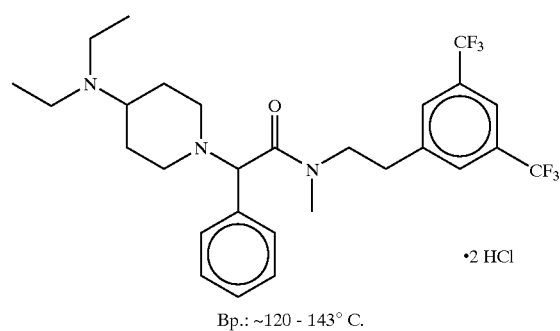
•2 HCl
Bp.: ~120 - 143° C.
EXAMPLE 16
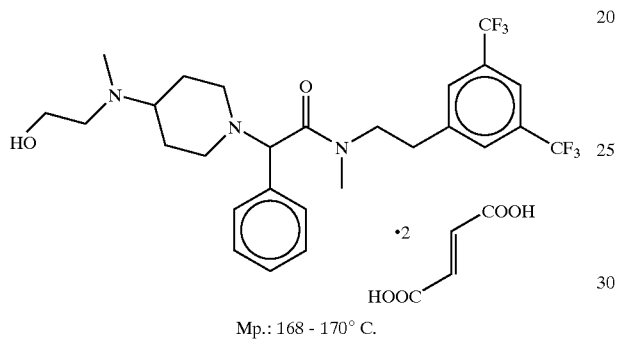
•2 fumaric acid
Mp.: 168 - 170° C.
EXAMPLE 17
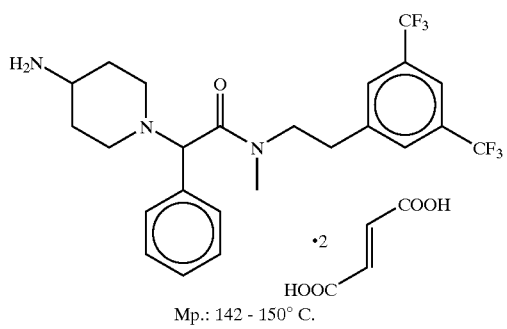
•2 fumaric acid
Mp.: 142 - 150° C.
EXAMPLE 18
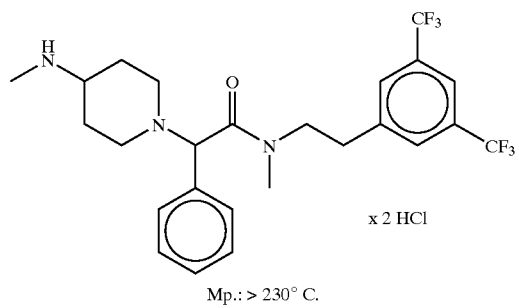
x 2 HCl
Mp.: > 230° C.
EXAMPLE 19
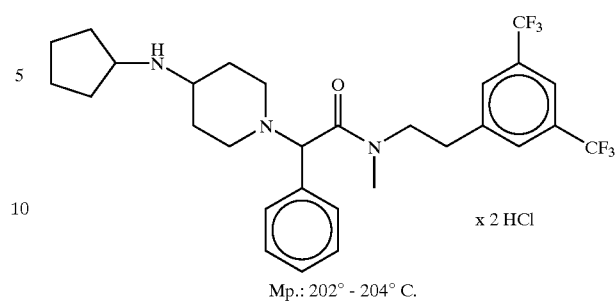
x 2 HCl
Mp.: 202° - 204° C.
EXAMPLE 20
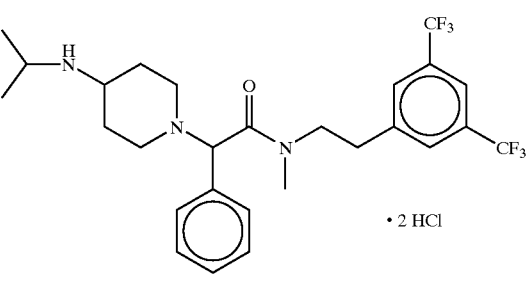
• 2 HCl
Mp.: 178° - 180° C.
EXAMPLE 22
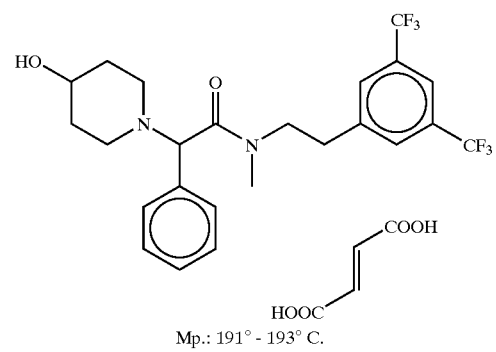
•fumaric acid
Mp.: 191° - 193° C.
EXAMPLE 23
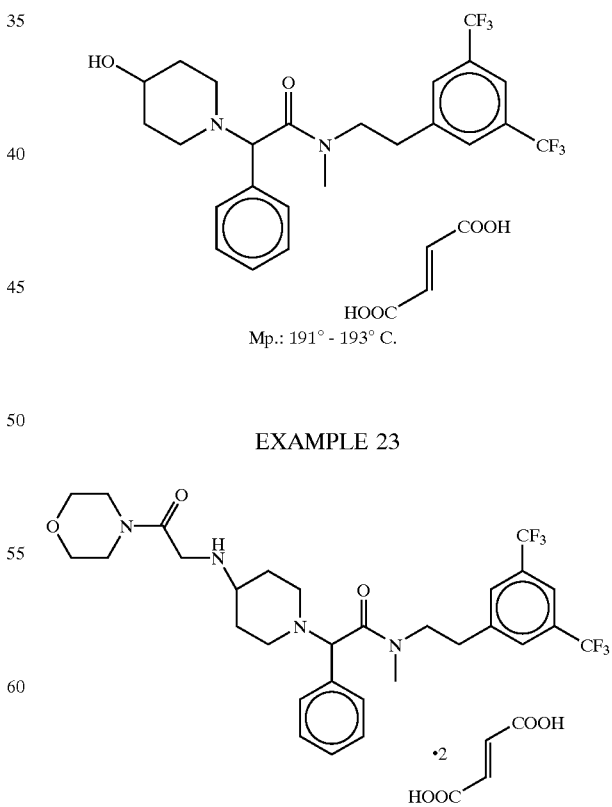
•2 fumaric acid
Mp.: 162–164° C.

EXAMPLE 24
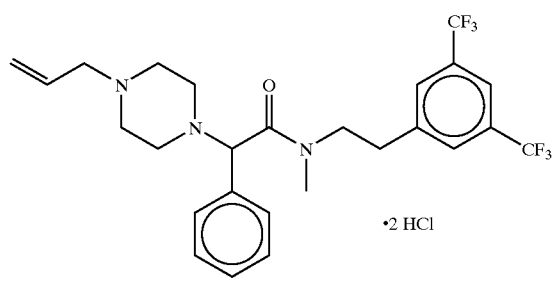
Mp.: 220–224° C. (Decomp.);
FAB-MS: (M+H)⁺ = 514.3
EXAMPLE 25
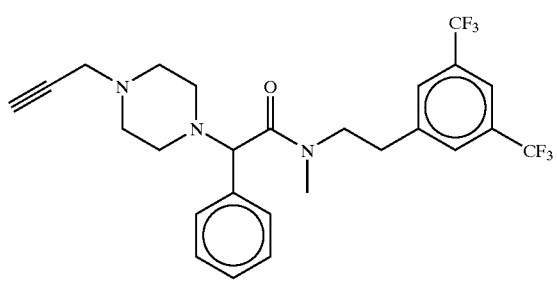
Mp.: 102–117° C.;
FAB-MS: (M+H)⁺ = 512.4
EXAMPLE 26
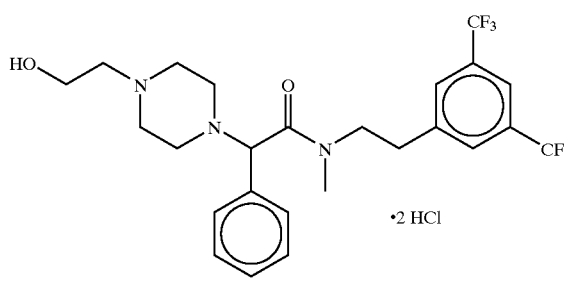
Mp.: 225°–232° C. (Decomp.);
FAB-MS: (M+H)⁺ = 518.3
EXAMPLE 27
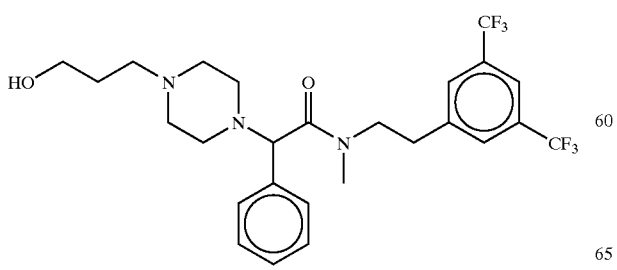
EXAMPLE 28
Mp.: 242–245° C. (Decomp.)
FAB-MS: (M+H)⁺ = 545.2
EXAMPLE 29
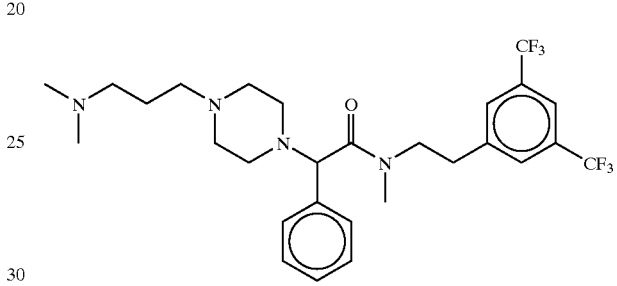
EXAMPLE 30
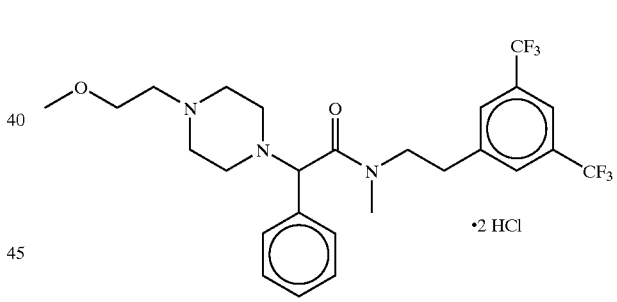
Mp.: 115°–124° C.;
FAB-MS: (M+H)⁺ = 532.3
EXAMPLE 31
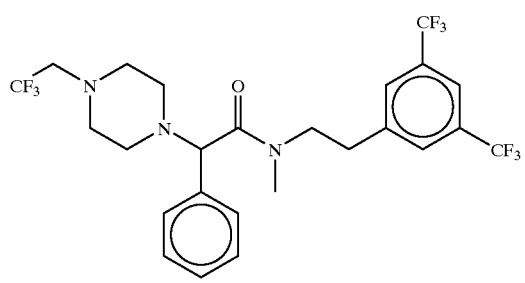

EXAMPLE 32
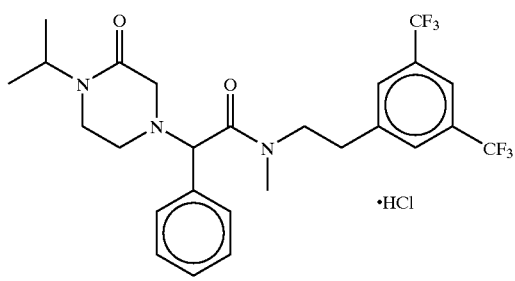
Mp.: 107–112° C.;
FAB-MS: (M+H)⁺ = 530.2
EXAMPLE 33
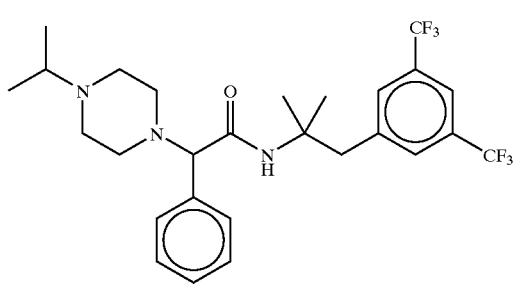
Mp.: 133–143° C.;
FAB-MS: (M+H)⁺ = 530.4
EXAMPLE 34
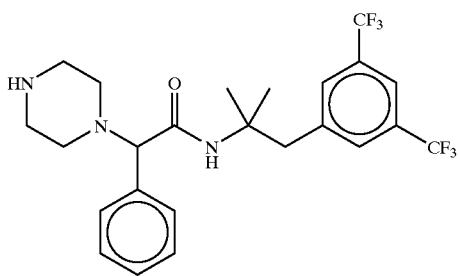
Mp.: 178–182° C.;
FAB-MS: (M+H)⁺ = 488.3
EXAMPLE 35
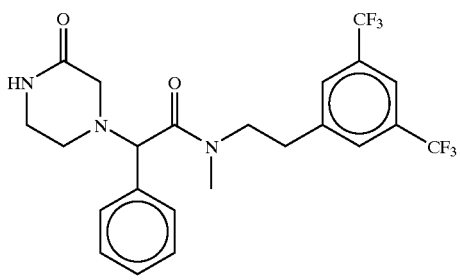
EXAMPLE 36
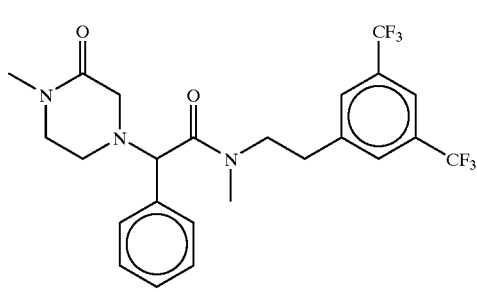
EXAMPLE 37
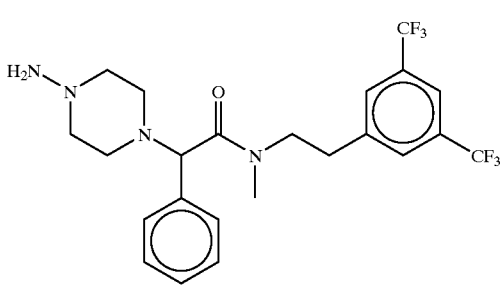
EXAMPLE 38
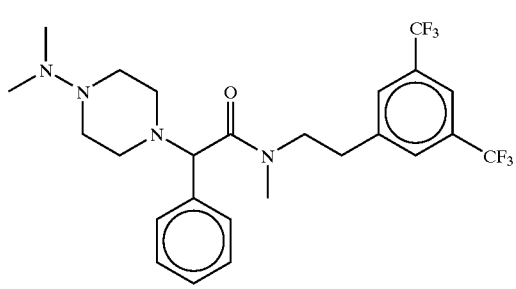
EXAMPLE 39
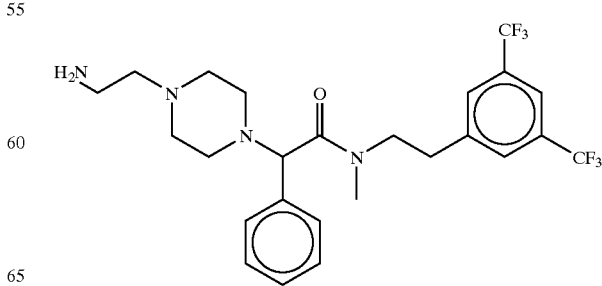

EXAMPLE 40
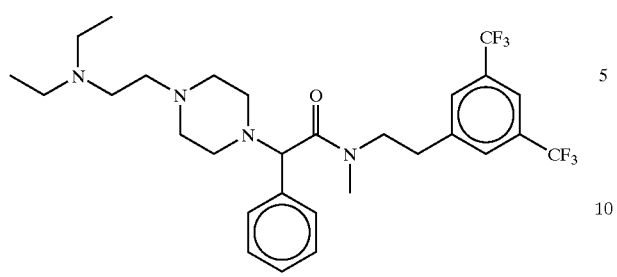
EXAMPLE 44
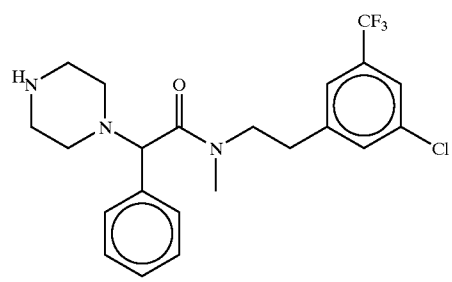
EXAMPLE 41
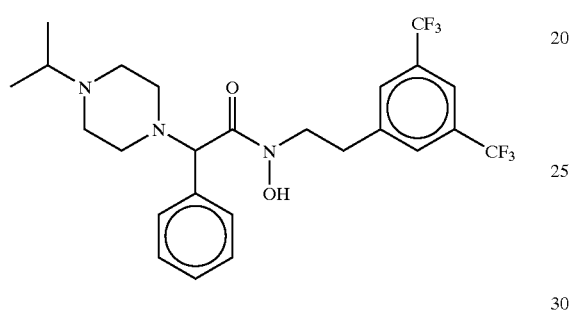
EXAMPLE 45
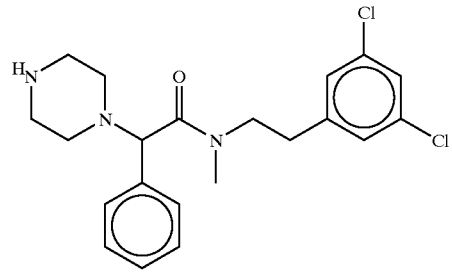
EXAMPLE 42
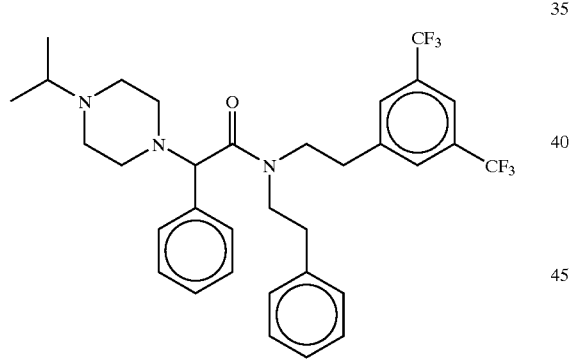
EXAMPLE 46
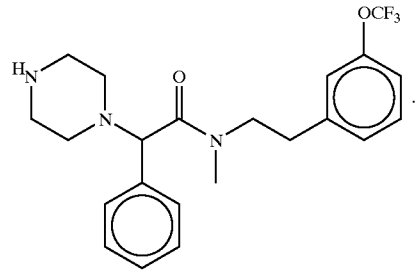
EXAMPLE 43
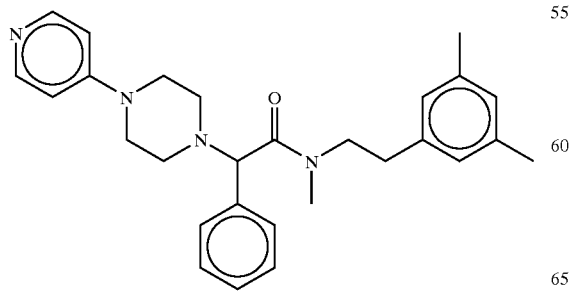
EXAMPLE 47
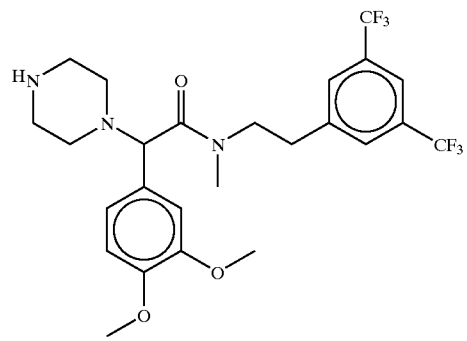
Mp.: 149–159° C.
FAB-MS: (M+H)$^+$ = 534.4

EXAMPLE 48
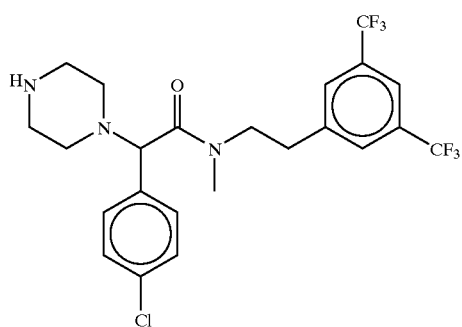
EXAMPLE 49
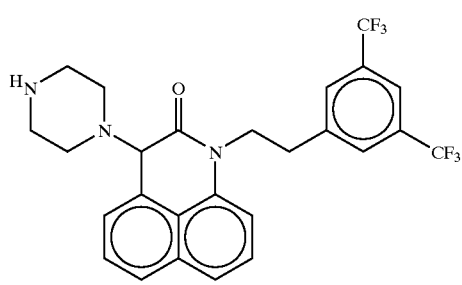
EXAMPLE 50
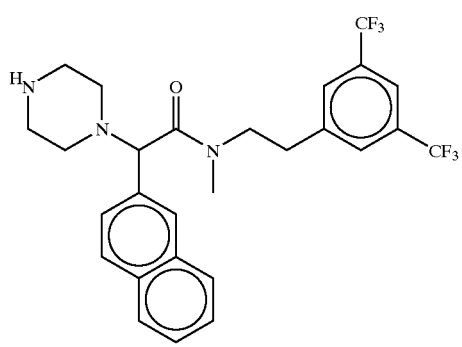
EXAMPLE 51
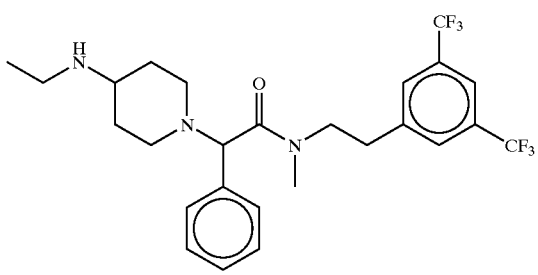
EXAMPLE 53
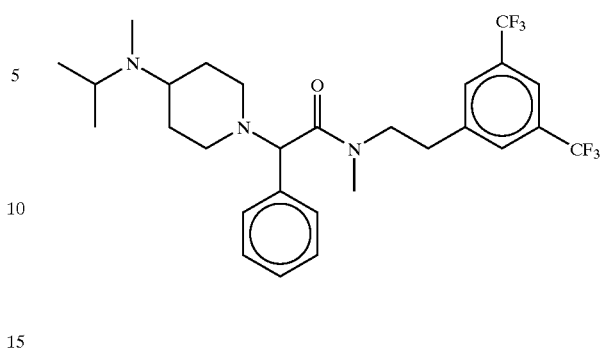
EXAMPLE 54
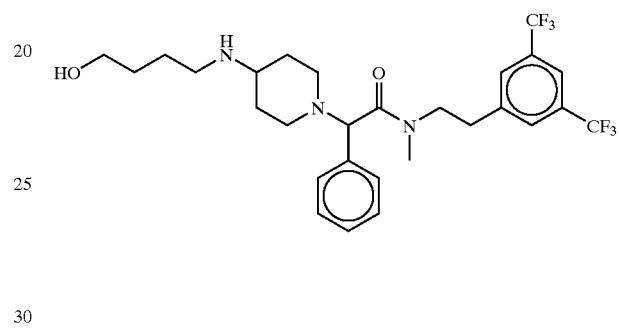
EXAMPLE 55
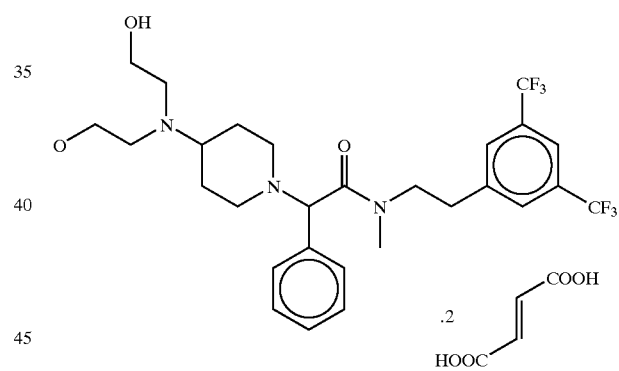
Mp.: 115–119° C.
EXAMPLE 56
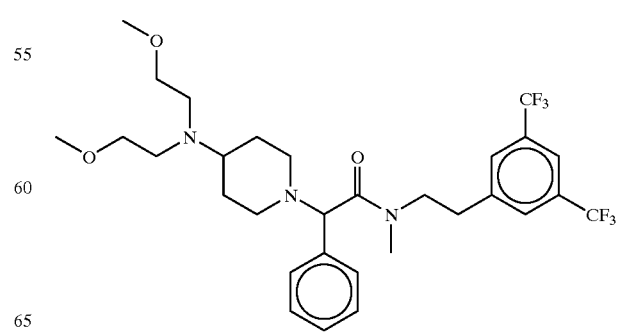

EXAMPLE 57
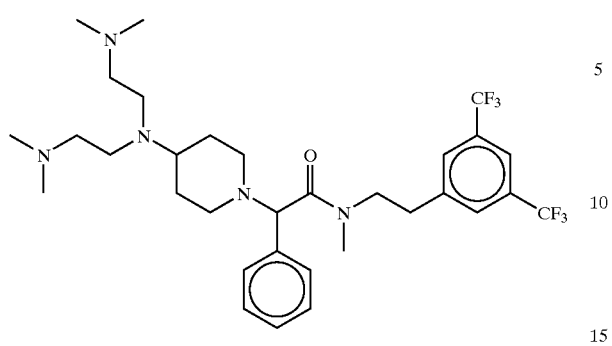
EXAMPLE 58
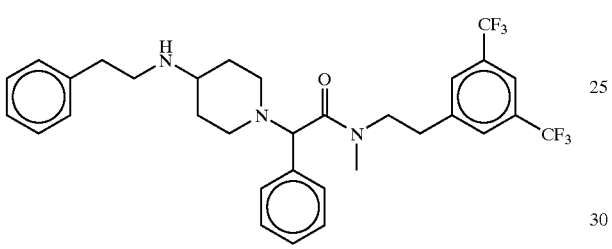
EXAMPLE 59
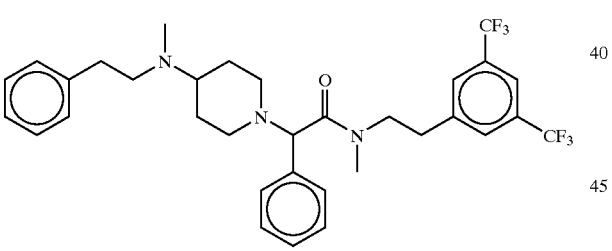
EXAMPLE 60
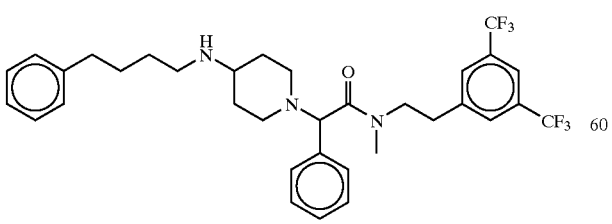
EXAMPLE 61
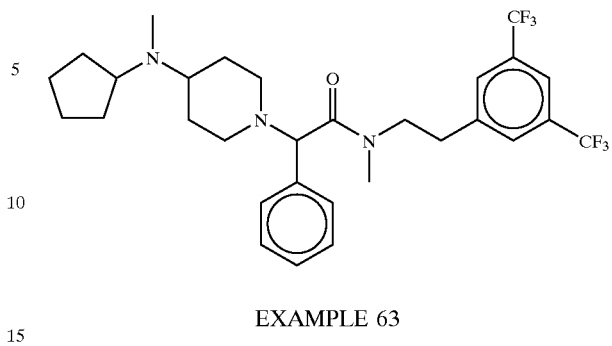
EXAMPLE 63
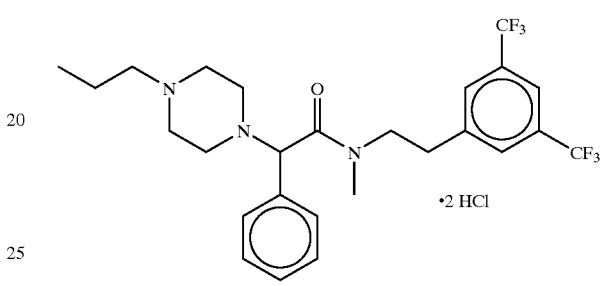
Mp.: 218–228° C. (Decomp.)
FAB-MS: $(M + H)^+ = 516.3$
EXAMPLE 64
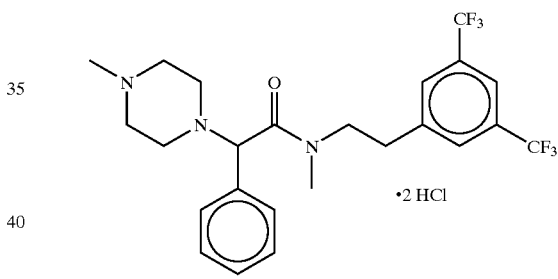
Mp.: 92–96° C.
FAB-MS: $(M + H)^+ = 488.2$
EXAMPLE 65
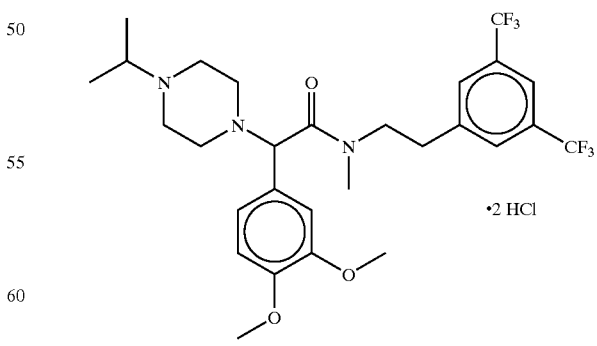
Mp.: 132–142° C.
FAB-MS: $(M + H)^+ = 576.5$

EXAMPLE 66
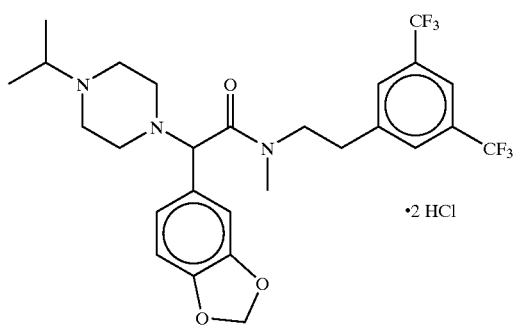
Mp.: 131–141° C.
FAB-MS: (M + H)⁺ = 560.1.
EXAMPLE 67
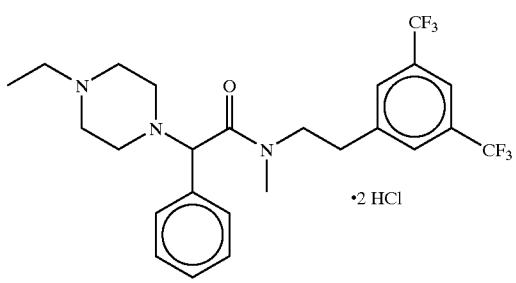
Mp.: 228–231° C. (Decomp.)
FAB-MS: (M + H)⁺ = 502.3
EXAMPLE 68
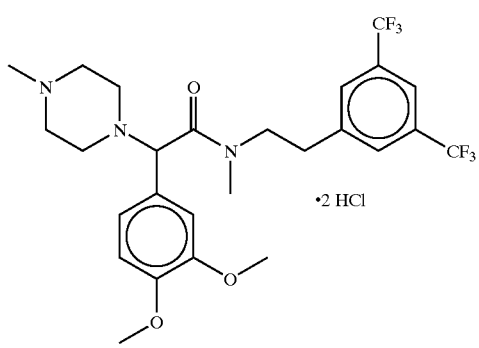
EXAMPLE 69
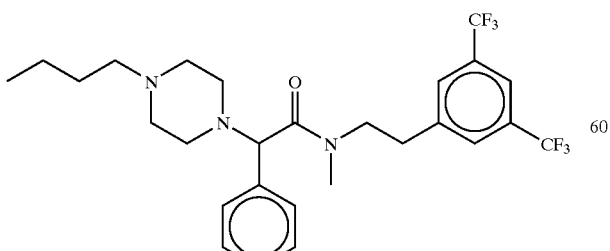
EXAMPLE 70
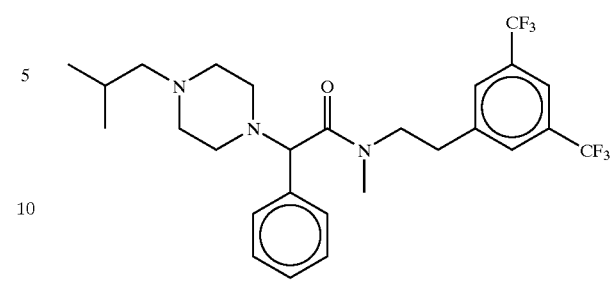
EXAMPLE 71
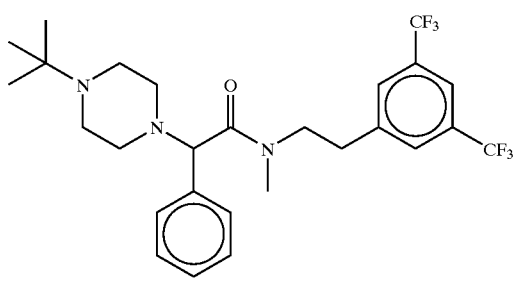
EXAMPLE 72
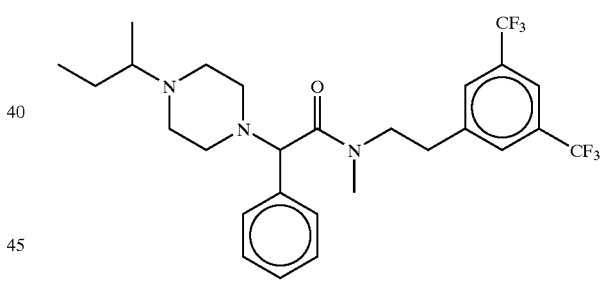
EXAMPLE 73
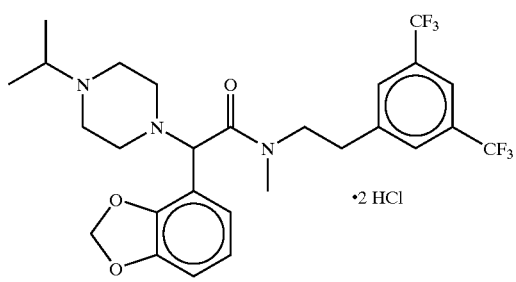
Mp.: 108–118° C.
FAB-MS: (M + H)⁺ = 560.4

EXAMPLE 74

Fp.: 138–148° C.
$[\alpha]_D^{20} = +45.5°$ (MeOH)
Mp.: 138–148° C.
$[\alpha]_D^{20} = +45.5°$ (MeOH)

EXAMPLE 75

Fp.: 166–176° C.
$[\alpha]_D^{20} = +19.0°$ (DMSO).
Mp.: 166–176° C.
$[\alpha]_D^{20} = +19.0°$ (DMSO)

EXAMPLE 76

Mp.: 132-134° C.

Of these compounds, the compounds of Examples 1 and 8 are preferred.

In the foregoing representations of the formulae, the $CH_3$ groups are not drawn in full.

Compound 1, for example, contains a methyl group as the group $R^5$.

Pharmaceutical Preparations
Injectable Solution
  200 mg of active substance*
  1.2 mg of monopotassium dihydrogen phosphate=$KH_2PO_4$)
  0.2 mg of disodium hydrogen phosphate=)(buffer) $Na_2HPO_4.2H_2O$)
  94 mg sodium chloride) (isotonic agents) or)
  520 mg glucose)
  4 mg albumin (protease protection)
  q.s. sodium hydroxide solution)
  q.s. hydrochloric acid) ad ph 6
  ad 10 ml water for injections
Injectable Solution
  200 mg active substance*
  94 mg sodium chloride or
  520 mg glucose
  4 mg albumin
  q.s. sodium hydroxide solution)
  q.s. hydrochloric acid) ad pH 9
  ad 10 ml water for injections
Lyophilisate
  200 mg of active substance*
  520 mg of mannitol (isotonic agent/framework agent)
  4 mg albumin
  Solvent 1 for lyophilisate
  10 ml of water for injections
  Solvent 2 for lyophilisate
  20 mg of Polysorbate®80=Tween®80 (surfactant)
  10 ml of water for injections
  * Active substance: compound according to the invention, e.g. one of examples 1 to 76
  Dosage for humans weighing 67 kg: 1 to 500 mg

What is claimed is:

1. A compound of Formula I wherein:
  Ar is an unsubstituted or mono- to penta-substituted phenyl, or unsubstituted or mono- or disubstituted naphthyl, wherein the substituents of the phenyl and naphthyl group of Ar independently of one another are selected from F, Cl, Br, I, $(C_{1-4})$alkyl, O—$(C_{1-4})$alkyl, $CF_3$, $OCF_3$, or $NR^{12}R^{13}$ wherein $R^{12}$ and $R^{13}$ independently of one another are H, methyl, or acetyl, or Ar is phenyl substituted by —O—$CH_2$—O— or —O—$(CH_2)_2$—O—;
  $R^1$ and $R^2$ together with the N to which they are bound are a ring of the formula $R^6$ is H, $(C_{1-5})$alkyl, $(C_{3-5})$alkenyl, propynyl, hydroxy$(C_{2-4})$alkyl, methoxy$(C_{2-4})$alkyl, di$(C_{1-3})$alkylamino$(C_{2-4})$ alkyl, amino($C_{2-4}$)alkyl, amino, di($C_{1-3}$)alkylamino, monofluoro- to perfluoro($C_{1-2}$)alkyl, N-methylpiperidinyl, pyridyl, pyrimidinyl, pyrazinyl, pyridazinyl, or the group —$CH_2$—C(O)$NR^{14}R^{15}$, wherein:

$R^{14}$ is H or ($C_{1-4}$)alkyl, and $R^{15}$ is H, ($C_{1-4}$)alkyl, ($C_{3-6}$)cycloalkyl, hydroxy($C_{2-4}$)alkyl, alkoxy($C_{2-3}$)alkyl, phenyl($C_{1-4}$)alkyl, or $R^{14}$ and $R^{15}$ together with the N to which they are bound form a 1-pyrrolidinyl, piperidino, morpholino, or 1-methylpiperazin-4-yl ring;

$R^9$ and $R^{10}$ independently of each other are ($C_{1-4}$)alkyl;

$R^{11}$ is H, ($C_{1-5}$)alkyl, ($C_{3-5}$)alkenyl, propynyl, hydroxy($C_{2-4}$)alkyl, methoxy($C_{2-3}$)alkyl, di($C_{1-3}$)alkylamino($C_{2-3}$)alkyl, amino($C_{2-3}$)alkyl, amino, di($C_{1-3}$)alkylamino, monofluoro- to perfluoro($C_{1-2}$)alkyl, N-methylpiperidinyl, pyridyl, pyrimidinyl, pyrazinyl, pyridazinyl or the group —$CH_2$—C(O)$NR^{23}R^{24}$, wherein $R^{23}$ and $R^{24}$ are defined as $R^{14}$ and $R^{15}$ hereinbefore;

$R^3$ is H or ($C_{1-4}$)alkyl;

$R^4$ is pheny($C_{1-4}$)alkyl or naphthyl($C_{1-4}$)alkyl, wherein phenyl is optionally substituted by 1 to 3 substituents, wherein the substituents independently of one another are F, Cl, Br, I, ($C_{1-4}$)alkyl, O—($C_{1-4}$)alkyl, $CF_3$, $OCF_3$, or $NR^{27}R^{28}$ wherein $R^{27}$ and $R^{28}$ independently of one another are H, methyl, or acetyl; and $R^5$ is H, ($C_{1-4}$)alkyl, ($C_{3-6}$)cycloalkyl, $CH_2COOH$, $CH_2C(O)NH_2$, OH or phenyl($C_{1-4}$)alkyl, or a pharmaceutically acceptable salt thereof.

2. The compound according to claim 1, wherein:

Ar is unsubstituted or mono- or disubstituted phenyl, or unsubstituted naphthyl, or Ar is phenyl substituted by —O—$CH_2$—O— or —O—($CH_2$)$_2$—O—;

$R^3$ is H or ($C_{1-4}$)alkyl;

$R^4$ is phenyl($C_{1-4}$)alkyl or naphthyl($C_{1-4}$)alkyl, wherein phenyl is optionally substituted by 1 or 2 substituents, wherein the substituents independently of one another are F, Cl, Br, I, ($C_{1-4}$)alkyl, O—($C_{1-4}$)alkyl, $CF_3$, or $OCF_3$; and $R^5$ is H, ($C_{1-4}$)alkyl, ($C_{3-6}$)cycloalkyl, OH, or phenyl($C_{1-4}$)alkyl.

3. The compound according to claim 1, wherein:

Ar is unsubstituted or mono- or disubstituted phenyl, or unsubstituted naphthyl, wherein the substituents of the phenyl independently on one another are F, Cl, Br, I, methyl, methoxy, $CF_3$, or $OCF_3$, or Ar is phenyl substituted by —O—$CH_2$—O— or —O—($CH_2$)$_2$—O—.

4. The compound according to claim 3, wherein:

Ar is phenyl, naphthyl, phenyl substituted by F, Cl, Br, I, or methoxy in position 3 and/or 4, or phenyl wherein positions 2 and 3 or 3 and 4 are linked by —O—$CH_2$—O—.

5. The compound according to claim 4, wherein:

Ar is phenyl, phenyl substituted by methoxy in positions 3 and 4, or phenyl in which positions 3 and 4 or 2 and 3 are linked by —O—$CH_2$—O—.

6. The compound according to claim 1, wherein $R^1$ and $R^2$ together with the N to which they are bound are the ring of the formula

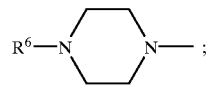

$R^6$ is H, ($C_{1-5}$)alkyl, ($C_{3-5}$)alkenyl, propynyl, hydroxy($C_{2-4}$)alkyl, methoxy($C_{2-4}$)alkyl, di($C_{1-3}$)alkylamino($C_{2-4}$)alkyl, amino($C_{2-4}$)alkyl, amino, di($C_{1-3}$)alkylamino, monofluoro- to perfluoro($C_{1-2}$)alkyl, N-methylpiperidinyl, pyridyl, pyrimidinyl, or

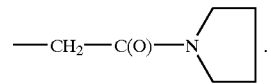

7. The compound according to claim 6, wherein $R^6$ is methyl.

8. The compound according to claim 6, wherein:

$R^6$ is H, ($C_{1-4}$)alkyl, propenyl, propynyl, hydroxy($C_{2-3}$)alkyl, methoxyethyl, di($C_{1-2}$)alkylamino($C_{2-3}$)alkyl, aminoethyl, amino, dimethylamino, $CH_2CF_3$, N-methylpiperidinyl, pyridyl, pyrimidinyl, or

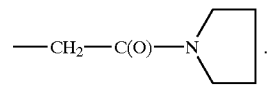

9. The compound according to claim 8, wherein:

$R^6$ is H, ($C_{1-3}$)alkyl, allyl, 2-propynyl, $CH_2CH_2OH$, —$CH_2CH_2OCH_3$, —$CH_2CH_2N(CH_3)_2$, N-methylpiperidinyl, 2-pyrimidinyl, or

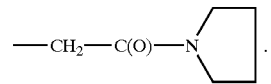

10. The compound according to claim 9, wherein:

$R^6$ is H, $CH_3$, $C_3H_7$, $CH(CH_3)_2$, $CH_2CH_2OH$, $CH_2CH_2OCH_3$, or $CH_2CH_2N(CH_3)_2$.

11. The compound according to claim 1, wherein:

$R^1$ and $R^2$ together with the N to which they are bound are the ring of the formula

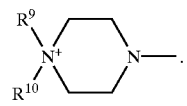

12. The compound according to claim 11, wherein Ar is phenyl substituted by —O—$CH_2$—O— or —O—($CH_2$)$_2$—O—.

13. The compound according to claim 11, wherein:

Ar is an unsubstituted or mono- to penta-substituted phenyl, wherein the substituents of the phenyl group of Ar independently of one another are selected from F, Cl, Br, I, ($C_{1-4}$)alkyl, O—($C_{1-4}$)alkyl, $CF_3$, $OCF_3$, or $NR^{12}R^{13}$ wherein $R^{12}$ and $R^{13}$ independently of one another are H, methyl, or acetyl.

14. The compound according claim 1, wherein $R^1$ and $R^2$ together with the N to which they are bound are the ring of the formula

15. The compound according claim 1, wherein:
R¹ and R² together with the N to which they are bound are the ring of the formula

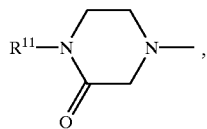

wherein $R^{11}$ is H or $(C_{1-3})$alkyl.

16. The compound according to claim 15, wherein $R^{11}$ is —CH(CH₃)₂.

17. The compound according claim 1, wherein $R^3$ is H.

18. The compound according to claim 1, wherein:
$R^4$ is phenyl$(C_{1-4})$alkyl, wherein phenyl is optionally substituted by 1 or 2 substituents, in which the substituents independently of one another are F, Cl, Br, I, $(C_{1-4})$alkyl, O—$(C_{1-4})$alkyl, CF₃, or OCF₃; and
$R^5$ is H, $(C_{1-4})$alkyl, $(C_{3-6})$cycloalkyl, —OH, or phenyl$(C_{1-4})$alkyl.

19. The compound according to claim 18, wherein:
$R^4$ is phenyl$(C_{2-4})$alkyl, wherein the substituents are in positions 3 and/or 5 of the phenyl ring; and
$R^5$ is H, methyl, OH, or phenethyl.

20. The compound according to claim 19, wherein: $R^4$ is

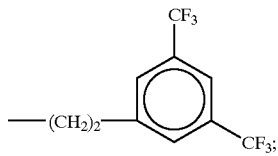

and $R^5$ is methyl.

21. A pharmaceutical composition of matter comprising a compound according to claim 1 and one or more pharmaceutically acceptable excipients or carriers.

22. A method of treating inflammatory and allergic diseases of the respiratory tract selected from asthma, chronic bronchitis, hyperreactive respiratory tract, emphysema, rhinitis, and cough in a warm-blooded animal, the method comprising administering to the animal a therapeutically effective amount of the compound according to claim 1.

23. A method of treating diseases of the central nervous system selected from dementia, Alzheimer's disease, schizophrenia, psychosis, depression, headache, epilepsy, Parkinson's disease, and stroke in a warm-blooded animal, the method comprising administering to the animal a therapeutically effective amount of the compound according to claim 1.

* * * * *